United States Patent [19]

Felix et al.

[11] Patent Number: 4,948,260
[45] Date of Patent: Aug. 14, 1990

[54] METHOD AND APPARATUS FOR EXAMINING HAIRINESS OF YARN

[75] Inventors: Ernst Felix, Uster; Hans Wampfler, Zurich, both of Switzerland

[73] Assignee: Zellweger Uster Ltd., Uster, Switzerland

[21] Appl. No.: 320,828

[22] Filed: Feb. 7, 1989

Related U.S. Application Data

[63] Continuation of Ser. No. 939,692, Dec. 9, 1986, abandoned.

[30] Foreign Application Priority Data

Dec. 17, 1985 [CH] Switzerland .................. 05 370/85

[51] Int. Cl.⁵ .......................................... G01B 11/00
[52] U.S. Cl. .................................. 356/429; 250/571
[58] Field of Search .................. 356/238, 429, 430; 250/571, 572

[56] References Cited

U.S. PATENT DOCUMENTS

| | | | |
|---|---|---|---|
| 2,641,960 | 6/1953 | Strother | 356/429 X |
| 2,699,701 | 1/1955 | Strother | 356/429 X |
| 2,991,685 | 7/1961 | Van Dongeren | 356/429 |
| 3,563,660 | 2/1971 | Solowey et al. | 356/336 |
| 3,709,610 | 1/1973 | Kruegle | 356/384 |
| 3,712,743 | 1/1973 | Harris et al. | 356/430 |
| 3,719,425 | 3/1973 | Leitz et al. | 356/430 |
| 3,804,529 | 4/1974 | Hansler | 356/429 |

FOREIGN PATENT DOCUMENTS

| | | | |
|---|---|---|---|
| 75791 | 11/1982 | | |
| 2637195 | 2/1978 | Fed. Rep. of Germany | 356/238 |
| 2123550 | 2/1984 | United Kingdom | 356/385 |

*Primary Examiner*—Richard A. Rosenberger
*Attorney, Agent, or Firm*—Burns, Doane, Swecker & Mathis

[57] ABSTRACT

The yarn (3) is illuminated by a transmitter (1) and the light reflected by the yarn surface is fed to a detector (5) and evaluated, the optical path being selected such that the receiver (5) receives light only from that side of the yarn (3) that is not illuminated.

10 Claims, 3 Drawing Sheets

METHOD AND APPARATUS FOR EXAMINING HAIRINESS OF YARN

This application is a continuation of application Ser. No. 939,692 filed Dec. 9, 1986 now abandoned.

The invention concerns a procedure to determine the surface structure of an extended testpiece, especially to measure yarn hairiness, in which the testpiece is illuminated by a transmitter and the light, which reflects from the surface to be examined and is influenced by the structure of such surface, is fed to a detector and evaluated.

In a procedure of this general type described in the Portuguese Patent No. 75791, the yarn is illuminated with monochromatic laser light, and the light emitted from the thread is fed to the receiver, which is placed in the main path of the rays. In the focal point of the receiver lens, a Fourier-diaphragm is placed, which absorbs the direct light, so that only the light diffracted from the standing fibers reaches the receiver. The measured light intensity is in proportion to the number of fibers standing up on the yarn surface and, therefore, is a measure of its hairiness.

The laser, which is needed for this procedure, due to the required light intensity, represents a considerable limitation; if a laser diode (or semiconductor laser) is used, it is difficult to handle and can be destroyed by static charges, overvoltages or reversed voltages. In addition, standard laser diodes are expensive. Gas lasers are also expensive, require a considerable installation length, and cannot be high-modulated. Because the laser light can damage the eyes, special precautions must be taken during the assembly and operation. Ultimately, the Fourier-diaphragm must be centered very exactly, which means an additional expenditure of time.

With the invention, a procedure of the type mentioned at the beginning shall now be indicated, which requires neither a laser nor exactly centered diaphragms.

According to the invention, this task is solved by choosing the optical path so that the detector is fed with light originating solely from the unlighted side of the testpiece.

In this way, only light from the illuminated edge of the testpiece surface impinges upon the receiver, and neither a laser nor a Fourier-diaphragm is required.

According to a preferred development of the procedure according to the invention, the light fed to the detector does not contain light from any parts of the optical elements placed in the transmitter's path of rays.

This means the receiver cannot see the optical elements placed in the transmitter's optical path, so that the scattered light from the dust particles cannot fall on the receiver.

On the other hand, according to the procedure described in the aforementioned Portuguese patent, the receiver is placed in the optical axis of the transmitter. This means that each dust particle lying on one of the optical elements in the transmitter's path of rays, such as lenses, mirrors or glass plates, generates scattered light and leads to errors in the measured value. This is due to the fact that this scattered light falls on the receiver and is measured as increased hairiness. This procedure, is, therefore, very susceptible to contamination and requires a substantially dust-free and clean environment, which represents a considerable limitation, especially for the processing and/or testing of textile threads.

In the procedure according to the invention, dust and dirt particles on the type glass and mirror elements do not result in an erroneous measured value. Instead they only lead to a minimal reduction of the light intensity, due to absorption. Therefore, the need for a clean environment and maintaining cleanliness are not as great.

At the same time, the procedure, according to the invention, has all the advantages of the procedure described in the aforementioned Portuguese Patent. This means that, during the measurement, one receives a continuous analog signal and can, therefore, continuously record the hairiness index. In addition, one receives a signal, which is independent of the draw-off speed of the yarn.

The invention also concerns a device to execute the mentioned procedure with a transmitter and a detector.

The device, according to the invention, is characterized by the fact that the path of rays is laid out so that the detector only receives light from the side of the testpiece that is not illuminated by the transmitter and, therefore, only receives light from the illuminated edge of the testpiece surface.

In the following, the invention is explained in greater detail, based on forms of construction and illustrations.

DETAILED DESCRIPTION OF THE INVENTION

Figure 1:
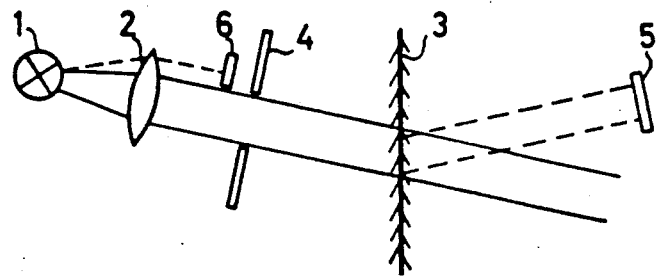
FIG. 1 to 6 each shows a diagrammatic representation of a form of construction of a device according to the invention.

The forms of construction depicted in FIG. 1 to 6 each show a sensing or measuring arrangement with a light source or transmitter 1 and a condenser lens 2 or lens which produces a beam of substantially parallel light rays at the transmitting end, which light from the transmitter 1 is directed at a yarn 3, the hairiness of which is to be measured. The scattered light from yarn 3 potted through a diaphragm 4 which defines the field to be measured, and hits an optical detector 5.

Important for the forms of construction represented is the evaluation, with the help of so-called dark field optics, of the light emitted from the yarn 3, caused by diffuse scattering, refraction, diffraction and/or reflection. In other words, this means that the detector 5 does not see the side of the yarn 3 which side is illuminated by the transmitter 1, and thus the detector 5 only receives light from the unlighted side of the yarn 3. This light at the unlighted side of the yarn is that which emanates from fiber fragments which protrude outwardly at the edges of the yarn and it constitutes a measure of the hairiness of the yarn.

The light picked up by the detector 5 is, therefore, independent of the yarn diameter and the diffuse light reflected back from the illuminated surface of the yarn 3 cannot impinge upon the detector 5, so that this detector only sees the luminous edge of the yarn. A continuous analog signal originates in the detector 5, so that the hairiness of the yarn 3 can be continuously recorded. In this case, only the scattered light reaches the detector 5, which is diffusely scattered, reflected and refracted on the fibers standing up on the edge of the yarn 3 — which are responsible for the hairiness — and, the intensity of this light is, as described in Portuguese Patent No. 75791, in proportion to the number of fibers standing up, and therefore, to the hairiness of the yarn.

Figure 3:
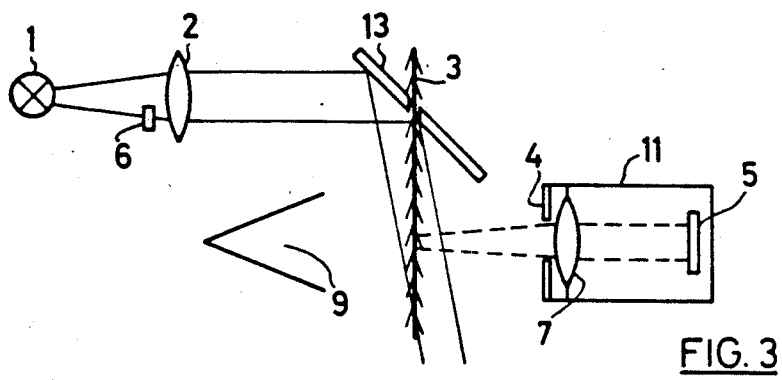

In the forms of construction of FIGS. 1 and 3 the detector 5 "cannot see" any optical elements, such as lenses or mirrors situated in the optical path of the transmitter 1 (i.e., placed between the transmitter 1 and the yarn 3). Therefore, the scattered light from the dust particles lying on these elements cannot fall directly on the detector 5. These dust and dirt particles absorb part of the light from the transmitter 1 and thereby produce a certain minimal reduction of the light intensity impinging upon the detector 5. However, such minimal absorption by the dust and dirt particles does not produce an erroneous measurement.

For the transmitter 1, an infrared light diode (IRED) is preferably used with the light of the diode preferably being modulated. This is so that, in the detector path, the ambient light can be filtered out with, for example, a bandpass filter. Also, it is advantageous to shield the ambient light somewhat. It goes without saying that the transmitter 1 could also comprise a visible LED, a laser, or some other light source instead of the infrared light diode.

The receiver 5 may be a large surface photodiode, to receive the most scattered light possible, and to be as independent as possible from the shifting of the yarn image caused by changes in position or yarn vibrations. The receiver 5 may also be a photo-multiplier, or a CCD-series cell (charge-coupled device), on which the yarn forms an image. In the latter case, one can measure the distribution of the hairiness in its distance from the edge of the yarn and thereby determine the diameter of the yarn 3.

Figure 2:
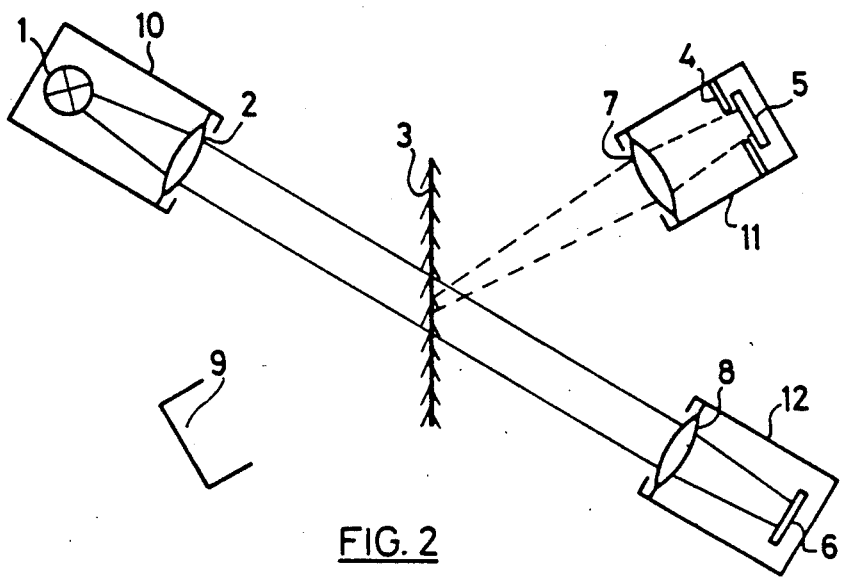

In the forms of construction of FIGS. 1 to 3, a reference diode 6 may be provided at the transmitter 1 and at the detector 5 (not shown) to compensate for temperature drift.

In FIG. 1, the simplest construction form is depicted, which does not use any lenses on the receiving side which, on the one hand means a certain cost reduction, however, on the other hand, leads to a relatively low light intensity on detector 5. The diaphragm 4 which defines the field of the measurement (i.e., a measuring field diaphragm) is placed on the transmitter side and the reference diode 6 is situated between the condenser lens 2 and the measuring field diaphragm 4.

In the form of construction depicted in FIG. 2, a lens amount of light which is directed to the detector 5. The amount of light which is directed to the detector 5. In image plane of the lens 7, a measuring field diaphragm 4 is situated. The reference diode 6 is placed in an extension of the optical axis of the transmitter side in a special reference path, which, in addition, has a lens 8. In the extension of the optical axis on the receiver side, there is provided a dark background 9 on the transmitter side of yarn 3, towards which the detector 5 is directed.

All optical elements are placed in overpressure containers 10, 11 and 12 (i.e., which are supplied with air so as to have an outflow of air) which prevents dust and dirt from penetrating. Due to the chosen arrangement, by no means whatever can scattered light from the lenses 2 and/or 8 fall directly on the detector 5. As a protection against the action of dust and/or dirt, appropriate air curtains (not shown) can also be used.

When the yarn 3 is removed from the device, the reference diode 6 serves to compensate for temperature and/or aging effects. When the yarn 3 is inserted, the optical yarn diameter can be determined.

While in the forms of construction of FIGS. 1 and 2, the light impinges upon the yarn 3 at an angle of approximately between 45 degrees and 70 degrees, the form of construction of FIG. 3 shows a very flat impact angle of approximately 0 degree to 20 degrees. This is made possible by a mirror 13, which has a slit, through which the yarn 3 is led. The ambient light is softened by a dark background 9 and by a detector casing 11, whereby the latter serves at the same time as an overpressure chamber to prevent the action of dust and dirt. The measuring field diaphragm 4 is situated on the detector side near the yarn 3 and the reference diode 6 is situated on the transmitter side.

Figure 4:
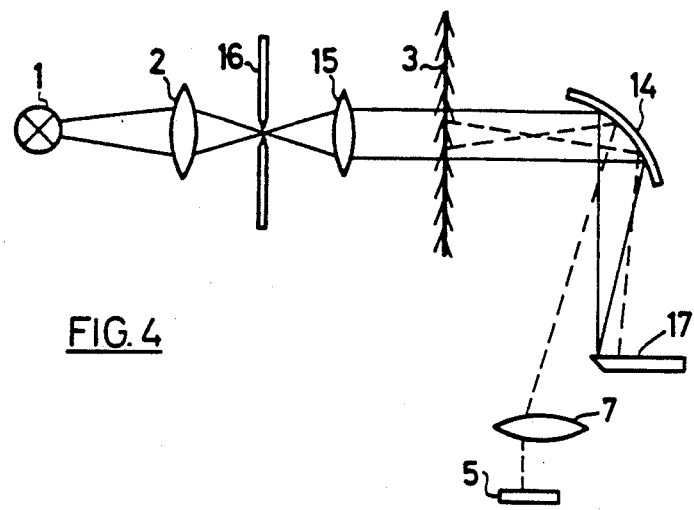

In FIG. 4 a form of construction with a schlieren arrangement is depicted, which has an image-forming deflection mirror 14 placed on the detector side. On the transmitter side, a second lens 15 is situated, after the condenser lens 2, and in its focal plane, there is a slit diaphragm 16 between these lenses. The slit diaphragm 16 forms an image on the edge 17, which acts as a diaphragm, which means that it is on a conjugate plane to it.

While the direct light is blocked by the edge 17, a portion of the scattered light gets past the edge and arrives at receiver 5.

Figure 5:
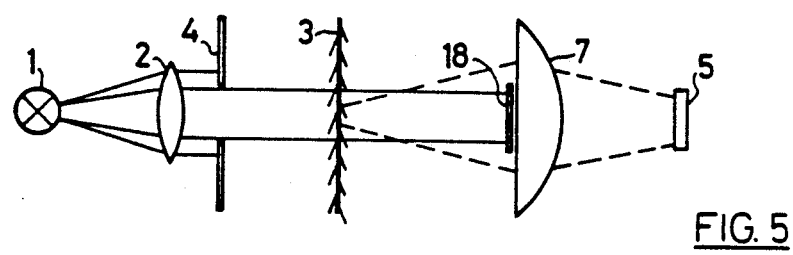
Figure 6:
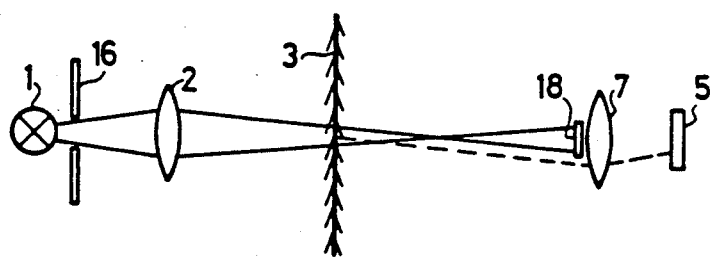

In conclusion, FIGS. 5 and 6 each show a form of construction for a dark field optics arrangement with a central diaphragm 18 to block the direct light. In the form of construction according to FIG. 5, the light emitted from the transmitter 1 leaves the condenser lens 2 as a parallel beam of rays and the measuring field diaphragm 4 is placed between the condenser lens 2 and yarn 3. The diaphragm 18, which absorbs the direct light rays, is placed directly in front of the receiver lens 7.

FIG. 6 shows a modification of this form of construction, in which a slit diaphragm 16 is placed between the transmitter 1 and condenser lens 2, and the central diaphragm 18 is placed in a conjugate plane to slit diaphragm 16, so that, through the condenser lens 2, the slit diaphragm 16 forms an image on the central diaphragm 18. The central diaphragm 18 is thereby situated directly in front of the receiver lens 7, Since, with this arrangement, the beam of rays from the condenser lens 2 and the receiver lens 7 does not run in a parallel manner, the signal of detector 5 is sensitive to the distance from yarn 3 to the receiver lens 7.

It is assumed that the average specialist is familiar with the actual evaluation of the signals of detector 5. Therefore, they have not been described in greater detail in the foregoing. In this connection, reference is made to the Portuguese Patent No. 75791 mentioned at the beginning, as well as to the brochure "Yarn Hairiness", Textile Progress, Volume 13, No. 1, The Textile Institute, Manchester.

The device described also contains, of course, mechanical components to insert and remove the yarn to be tested. Since, in principle, these mechanical components are the same as in the measuring instruments for hairiness available commercially today, which, by the way for the most part are based on a method of counting the fibers standing up from the yarn, it is also not described here. In this connection, reference is made to the brochure mentioned previously "Yarn Hairiness".

Figure 7:
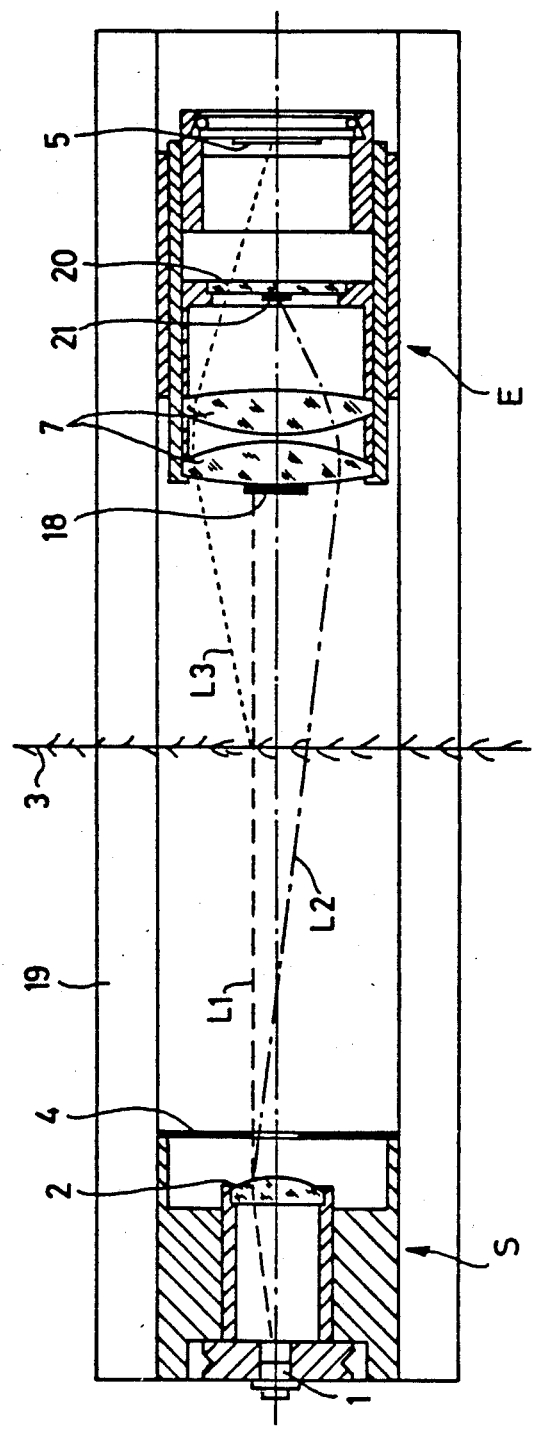
FIG. 7 shows an actual arrangement according to the configuration of FIG. 5.

FIG. 7 shows the design construction of a measuring arrangement of the type schematically represented in FIG. 5, in a scale of approximately 1:1. According to the representation, the measuring device consists of two subassemblies, a transmitter component S and a detector component E, which are assembled on a base plate 19. Besides a light emitting diode serving as the transmitter 1, the transmitter component S contains a condenser lens 2, which combines the light from the light emitting diode into a parallel beam of rays, as well as the measuring field diaphragm 4.

The detector component E contains the center 7 with the central diaphragm 18 and the detector 5. Between the center 7 and the detector 5, a glass holder 20 is placed with an absorber diaphragm 21.

The beam of rays L1 emitted from the light emitting diode 1, which is limited by the measuring field diaphragm 4, is blocked by the central diaphragm 18. From the light scattered by dust possibly lying on condenser lens 2, a ray of light L2 reaches the detector component E, and goes outside of the central diaphragm 18 through center 7, and will, however, be blocked by the absorber diaphragm 21. So, in the end, only the light L3 scattered on yarn 3 impinges upon detector 5.

Since a great deal of dust is created when yarn is measured, a number of corrective measures have been taken in the measuring device depicted in FIG. 7 to reduce the influence of dust on the measurement. The distance from condenser lens 2 and center 7 to the yarn 3 is large. The central diaphragm 18 prevents glass particles from the center 7 from lying in the direct path of rays. Therefore, no scattered light is generated by the dust particles on the center 7. And, by the center 7, the condenser lens 2 forms an image on the absorber diaphragm 21. In this way, any scattered light, which might eventually be generated on condenser lens 2, will be blocked and cannot reach detector 5.

In practical applications, the depicted measuring device will be installed in an instrument, which, among other things, will have guiding and transport means for the yarn; see, for example, the Swiss Patent Application No. 02 823/86-2, the entire disclosure of which is incorporated herein by reference. In the running direction of the yarn 3, that is in FIG. 7 from the top to the bottom, a tension device is placed in front of the measuring organ, in the upper part of the figure. In the area of the measuring device, shortly before and after the beam of rays, two thread guides are provided, and below the measuring device, two drawing-off rollers are provided for the yarn 3. The drawing-off speed may be up to several meters per second.

In order to eliminate disturbing influences caused by ambient light, the transmitter 1 is modulated. The photoelectric current generated in the detector 5 is converted into a proportional voltage and this signal is amplified, rectified, filtered through a low-pass filter and then evaluated by a computer. Thereby, the voltage averaged over time is a measure for the average hairiness index. However, short-term fluctuations of the hairiness or periods of hairiness can also be measured by applying the Fourier-transformation.

What is claimed is:

1. Apparatus for sensing the hairiness of yarn as such yarn is being fed lengthwise along a yarn path, said apparatus comprising
    light supplying means on one side of said yarn path for transmitting a beam of light along an optical path which intersects said yarn path, said light supplying means including a light transmitting component exposed at its outer surface to the atmosphere in the vicinity of said yarn path, and
    detector means on the side of said yarn path opposite to said light supplying means for receiving from the full extent of the luminous edges of said yarn an amount of light which is a function of the hairiness of said yarn, said detector means being out of said optical path of said beam and out of the path of light deflected by dust particles on said light transmitting component illuminated by said beam as it passes to said yarn path.

2. An apparatus for examining the surface structure of a long testpiece comprising:
    a lighting component for illuminating a testpiece to be examined, said lighting component comprising a transmitter and a first lens for illuminating a test piece to be examined with a collimated light beam;
    a detection component for receiving and evaluating light reflected by a surface of the testpiece and influenced by the structure of said surface, said detection component comprising a detector and a second lens;
    a first absorption diaphragm placed in front of the said second lens for screening the direct light from the illuminated side of the testpiece; and
    a second absorption diaphragm placed between the said second lens and the said detector for screening stray light from the said first lens.

3. The apparatus as set forth in claim 2, wherein an infrared light-emitting diode is used as said transmitter.

4. The apparatus as set forth in claim 2, wherein the light emitted by said transmitter is modulated.

5. The apparatus as set forth in claim 2, wherein said detector is formed by a photoelectric element such as a photodiode.

6. The apparatus as set forth in claim 2, wherein said detector is formed by a photomultiplier.

7. The apparatus as set forth in claim 2, wherein said detector is formed by a charge-coupled device.

8. The apparatus as set forth in claim 2, further comprising a reference means to compensate for temperature drift, and/or deterioration of the apparatus and/or a possible reduction of the light intensity at said means for detecting due to dirt collection within the apparatus.

9. Apparatus for sensing the hairiness of yarn as such yarn is being fed along a yarn path extending through a measuring gap, said apparatus comprising
    light supplying means on one side of said gap for transmitting a collimated beam of light across said gap along an optical path which intersects said yarn path, said light supplying means including a lens component exposed on its output surface to the atmosphere of said gap;
    first light blocking means beyond said yarn path in said optical path for blocking light from said light supplying means which is not deflected from said beam;
    light receiving lens means beyond said first light blocking means or receiving light deflected out of said beam by particles of foreign matter and by fiber fragments at the surface of the yarn;
    second light blocking means beyond said light receiving lens means, said light receiving lens means forming on said second light blocking means an image of said lens component of said light supplying means so that light deflected from said beam by particles of foreign matter on said exposed surface of said lens component will be blocked by said second light blocking means; and
    detector means beyond said second light blocking means, said light receiving lens means directing light deflected from said light beam by fiber fragments at the surface of said yarn onto said detector means so that the amount of light detected will provide an indication of the hairiness of the yarn.

10. A method for measuring the hairiness of a hairy yarn being fed lengthwise along a yarn path comprising:
illuminating the yarn from one side of said yarn path with a light beam from a transmitter having an output optical component exposed to the atmosphere adjacent said yarn path to provide said hairy yarn with luminous edge portions resulting from reflection of light from the hairy edge portions of said yarn, said luminous edge portions being visible on a side of said yarn path opposite to said one side;
collecting light from said yarn at the opposite side of said yarn path through the use of an optical system so disposed that it is not illuminated by direct light transmitted toward the yarn path;
blocking out that portion of the collected light attributable to stray light from foreign matter on said optical component; and
detecting the remainder of said collected light.

* * * * *